US008369964B2

(12) United States Patent
Ameri

(10) Patent No.: US 8,369,964 B2
(45) Date of Patent: Feb. 5, 2013

(54) MRI COMPATIBLE MEDICAL DEVICE LEAD INCLUDING TRANSMISSION LINE NOTCH FILTERS

(75) Inventor: Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 176 days.

(21) Appl. No.: 12/880,565

(22) Filed: Sep. 13, 2010

(65) Prior Publication Data
US 2011/0087302 A1    Apr. 14, 2011

Related U.S. Application Data

(60) Provisional application No. 61/250,395, filed on Oct. 9, 2009.

(51) Int. Cl.
*A61N 1/00* (2006.01)
(52) U.S. Cl. ........................................ 607/116
(58) Field of Classification Search .................. 607/116
See application file for complete search history.

(56) References Cited

U.S. PATENT DOCUMENTS

| 5,003,975 | A | 4/1991 | Hafelfinger et al. |
| 5,201,865 | A | 4/1993 | Kuehn |
| 5,370,666 | A | 12/1994 | Lindberg et al. |
| 5,476,485 | A | 12/1995 | Weinberg et al. |
| 5,534,018 | A | 7/1996 | Wahlstrand et al. |
| 5,549,646 | A | 8/1996 | Katz et al. |
| 5,727,552 | A | 3/1998 | Ryan |
| 5,727,553 | A | 3/1998 | Saad |
| 5,755,742 | A | 5/1998 | Schuelke et al. |
| 5,766,227 | A | 6/1998 | Nappholz et al. |
| 5,800,496 | A | 9/1998 | Swoyer et al. |
| 5,817,136 | A | 10/1998 | Nappholz et al. |
| 5,891,179 | A | 4/1999 | Er et al. |
| 6,016,447 | A | 1/2000 | Juran et al. |
| 6,101,417 | A | 8/2000 | Vogel et al. |
| 6,192,280 | B1 | 2/2001 | Sommer et al. |
| 6,317,633 | B1 | 11/2001 | Jorgenson et al. |
| 6,360,129 | B1 | 3/2002 | Ley et al. |
| 6,721,600 | B2 | 4/2004 | Jorgenson et al. |
| 6,949,929 | B2 | 9/2005 | Gray et al. |
| 6,999,818 | B2 | 2/2006 | Stevenson et al. |
| 7,013,180 | B2 | 3/2006 | Dublin et al. |
| 7,047,075 | B2 | 5/2006 | Stubbs |
| 7,047,083 | B2 | 5/2006 | Gunderson et al. |

(Continued)

FOREIGN PATENT DOCUMENTS

| EP | 1852810 B1 | 11/2007 |
| WO | WO2010078552 A1 | 7/2010 |

OTHER PUBLICATIONS

Basso, Christophe, "SPICE Model Simulates Spark-Gap Arrestor", Electronics Design, Strategy, and News (EDN), Jul. 3, 1997, 4 pages.

(Continued)

*Primary Examiner* — George Manuel
(74) *Attorney, Agent, or Firm* — Faegre Baker Daniels LLP

(57) ABSTRACT

A medical device lead includes a conductor and one or more band stop filters. The conductor extends through a lead body and includes a proximal end and a distal end. The one or more band stop filters each have a first end and a second end and include a conductive coil. At least one of the first end and second end of each band stop filter is coupled to the conductor. A length of each band stop filter is such that, at magnetic resonance imaging (MRI) frequencies, the band stop filter phase shifts an MRI-induced signal on the conductor by 180° to attenuate the MRI-induced signal on the conductor.

21 Claims, 6 Drawing Sheets

U.S. PATENT DOCUMENTS

| | | | |
|---|---|---|---|
| 7,050,855 | B2 | 5/2006 | Zeijlemaker et al. |
| 7,113,827 | B2 | 9/2006 | Silvestri et al. |
| 7,123,013 | B2 | 10/2006 | Gray |
| 7,135,978 | B2 | 11/2006 | Gisselberg et al. |
| 7,138,582 | B2 | 11/2006 | Lessar et al. |
| 7,174,219 | B2 | 2/2007 | Wahlstrand et al. |
| 7,174,220 | B1 | 2/2007 | Chitre et al. |
| 7,239,916 | B2 | 7/2007 | Thompson et al. |
| 7,289,851 | B2 | 10/2007 | Gunderson et al. |
| 7,369,898 | B1 | 5/2008 | Kroll et al. |
| 7,388,378 | B2 | 6/2008 | Gray et al. |
| 7,535,363 | B2 | 5/2009 | Gisselberg et al. |
| 7,630,761 | B2 | 12/2009 | Salo et al. |
| 7,953,499 | B2 | 5/2011 | Knapp et al. |
| 8,145,324 | B1 * | 3/2012 | Stevenson et al. ............ 607/122 |
| 2003/0028231 | A1 | 2/2003 | Partridge et al. |
| 2003/0083726 | A1 | 5/2003 | Zeijlemaker et al. |
| 2003/0093136 | A1 | 5/2003 | Osypka et al. |
| 2003/0140931 | A1 | 7/2003 | Zeijlemaker et al. |
| 2003/0144705 | A1 | 7/2003 | Funke |
| 2003/0144718 | A1 | 7/2003 | Zeijlemaker |
| 2003/0144719 | A1 | 7/2003 | Zeijlemaker |
| 2003/0144720 | A1 | 7/2003 | Villaseca et al. |
| 2003/0144721 | A1 | 7/2003 | Villaseca et al. |
| 2003/0204217 | A1 | 10/2003 | Greatbatch |
| 2004/0064161 | A1 | 4/2004 | Gunderson et al. |
| 2004/0172117 | A1 | 9/2004 | Hill et al. |
| 2005/0113676 | A1 | 5/2005 | Weiner et al. |
| 2005/0113873 | A1 | 5/2005 | Weiner et al. |
| 2005/0113876 | A1 | 5/2005 | Weiner et al. |
| 2005/0197677 | A1 | 9/2005 | Stevenson |
| 2005/0222656 | A1 | 10/2005 | Wahlstrand et al. |
| 2005/0222657 | A1 | 10/2005 | Wahlstrand et al. |
| 2005/0222658 | A1 | 10/2005 | Hoegh et al. |
| 2005/0222659 | A1 | 10/2005 | Olsen et al. |
| 2005/0267556 | A1 | 12/2005 | Shuros et al. |
| 2006/0030774 | A1 | 2/2006 | Gray et al. |
| 2006/0041294 | A1 | 2/2006 | Gray |
| 2006/0041296 | A1 | 2/2006 | Bauer et al. |
| 2006/0118758 | A1 | 6/2006 | Wang et al. |
| 2006/0247747 | A1 | 11/2006 | Olsen et al. |
| 2006/0247748 | A1 | 11/2006 | Wahlstrand et al. |
| 2006/0252314 | A1 | 11/2006 | Atalar et al. |
| 2006/0271138 | A1 | 11/2006 | MacDonald |
| 2007/0010702 | A1 | 1/2007 | Wang et al. |
| 2007/0027532 | A1 | 2/2007 | Wang et al. |
| 2007/0179577 | A1 | 8/2007 | Marshall et al. |
| 2007/0179582 | A1 | 8/2007 | Marshall et al. |
| 2007/0191914 | A1 | 8/2007 | Stessman |
| 2008/0033497 | A1 | 2/2008 | Bulkes et al. |
| 2008/0051854 | A1 | 2/2008 | Bulkes et al. |
| 2008/0057784 | A1 | 3/2008 | Zarembo et al. |
| 2008/0132985 | A1 | 6/2008 | Wedan et al. |
| 2008/0154348 | A1 | 6/2008 | Atalar et al. |
| 2008/0208290 | A1 | 8/2008 | Phillips et al. |
| 2009/0005825 | A1 | 1/2009 | MacDonald |
| 2009/0024180 | A1 | 1/2009 | Kisker et al. |
| 2009/0024197 | A1 | 1/2009 | Jensen |
| 2009/0149920 | A1 | 6/2009 | Li et al. |
| 2009/0149933 | A1 | 6/2009 | Ameri |
| 2009/0204171 | A1 | 8/2009 | Ameri |
| 2009/0210022 | A1 | 8/2009 | Powers |
| 2010/0103215 | A1 | 4/2010 | Iriguchi |
| 2010/0106215 | A1 | 4/2010 | Stubbs et al. |
| 2010/0125320 | A1 | 5/2010 | Polkinghorne et al. |
| 2011/0060394 | A1 | 3/2011 | Poore |
| 2011/0160816 | A1 | 6/2011 | Stubbs et al. |
| 2012/0143273 | A1 | 6/2012 | Stubbs et al. |

OTHER PUBLICATIONS

Partial International Search Report issued in PCT/US2011/052541, mailed Dec. 6, 2011, 4 pages.

File History for U.S. Appl. No. 11/015,807, filed Dec. 17, 2004.

International Search Report and Written Opinion issued in PCT/US2009/056843, mailed Dec. 29, 2009, 13 pages.

International Search Report and Written Opinion issued in PCT/US2010/048620, mailed Apr. 5, 2011, 10 pagaes.

"High Voltage Engineering and Testing, 2nd Edition", edited by Hugh M. Ryan, Institution of Engineering and Technology, 2001, 15 pages.

Citel Inc., Data Sheet, BH Series 2 Electrode Miniature Gas Discharge Tube Surge Arrester—8mm, May 14, 2009, 2 pages.

Hayes, David L., Chapter 4, "Generator and Lead Selection" from book entitled "Cardiac Pacing and Defibrillation A Clinical Approach", John Wiley & Sons, (c) 2000 Mayo Foundation, p. 129-157.

* cited by examiner

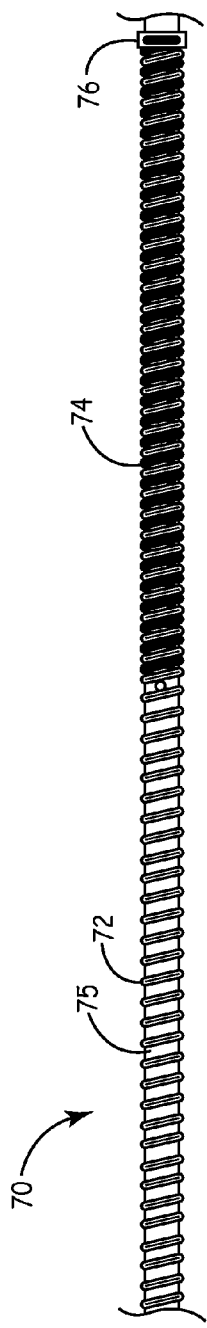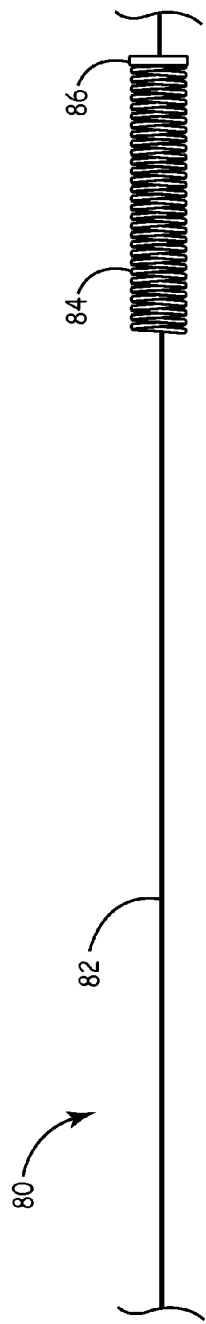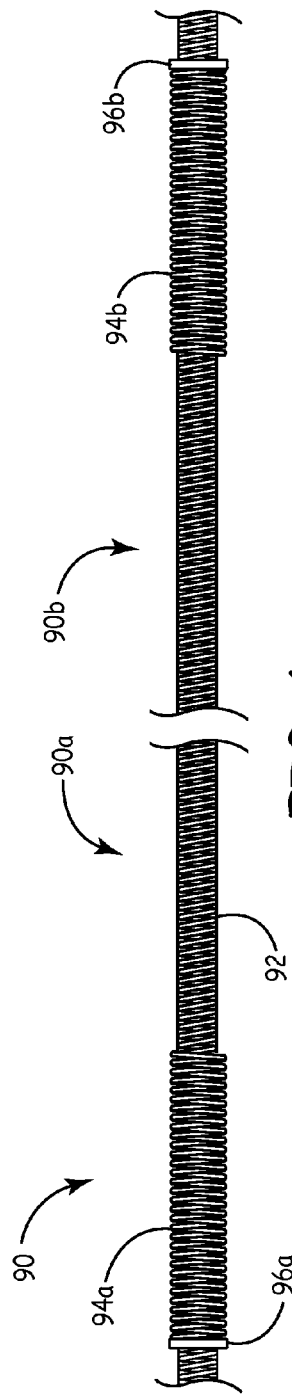

MRI COMPATIBLE MEDICAL DEVICE LEAD INCLUDING TRANSMISSION LINE NOTCH FILTERS

CROSS-REFERENCE TO RELATED APPLICATION

This application claims priority to Provisional Application No. 61/250,395, filed Oct. 9, 2009, which is herein incorporated by reference in its entirety.

TECHNICAL FIELD

The present invention relates to implantable medical devices. More particularly, the present invention relates to MRI compatible medical device lead constructions including transmission line notch filters.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are conductor assemblies for implantable medical electrical leads including one or more band stop filters, as well as medical electrical leads including such components.

In Example 1, a medical device lead includes a conductor extending through a lead body and including a proximal end and a distal end. The medical device lead also includes one or more band stop filters each having a first end and a second end and including a conductive coil. At least one of the first end and second end of each band stop filter is coupled to the conductor. A length of each band stop filter is such that, at magnetic resonance imaging (MRI) frequencies, the band stop filter phase shifts an MRI-induced signal on the conductor by 180° to attenuate the MRI-induced signal on the conductor.

In Example 2, the medical device lead according to Example 1, wherein at least one of the one or more band stop filters is coupled to the conductor at either the first end or the second end, and wherein the length of the at least one of the one or more band stop filters is about one quarter wavelength of the MRI-induced signal on the conductor.

In Example 3, the medical device lead according to either Example 1 or 2, wherein at least one of the one or more band stop filters is coupled to the conductor at both the first end and second end, and wherein the length of the at least one of the one or more band stop filters is about one half wavelength of the MRI-induced signal on the conductor minus a length to account for a propagation delay through the conductor between the first and second ends.

In Example 4, the medical device lead according to any of Examples 1-3, wherein the conductive coil of the band stop filter is coaxial with the conductor.

In Example 5, the medical device lead according to any of Examples 1-4, wherein the conductive coil of the band stop filter is co-radial with the conductor.

In Example 6, the medical device lead according to any of Examples 1-5, wherein the one or more band stop filters comprises at least two band stop filters configured to attenuate MRI-induced signals at different frequencies.

In Example 7, the medical device lead according to any of Examples 1-6, wherein at least one of the one or more band stop filters is proximate the distal end of the conductor.

In Example 8, a medical device lead includes a lead body including a conductor extending from a proximal end, which is configured to be connected to a pulse generator, to a distal end. The medical device lead also includes one or more band stop filters within the lead body each including a conductive element having a length, a first end, and a second end. At least a portion of the conductive element forms a conductive coil. Each band stop filter is coupled to the conductor such that an MRI-induced signal on the conductor propagates through the band stop filter a total distance of approximately one-half wavelength of the MRI-induced signal.

In Example 9, the medical device lead according to Example 8, wherein at least one of the one or more band stop filters is coupled to the conductor at either the first end or the second end, and wherein the length of the conductive element of the at least one of the one or more band stop filters is about one quarter wavelength of the MRI-induced signal on the conductor.

In Example 10, the medical device lead according to either Example 8 or 9, wherein at least one of the one or more band stop filters is coupled to the conductor at both the first end and second end, and wherein the length of the conductive element of the at least one of the one or more band stop filters is about one half wavelength of the MRI-induced signal on the conductor minus a length to account for a propagation delay through the conductor between the first and second ends.

In Example 11, the medical device lead according to any of Examples 8-10, wherein the conductive coil of the band stop filter is coaxial with the conductor.

In Example 12, the medical device lead according to any of Examples 8-11, wherein the conductive coil of the band stop filter is co-radial with the conductor.

In Example 13, the medical device lead according to any of Examples 8-12, wherein the one or more band stop filters comprises at least two band stop filters configured to attenuate MRI-induced signals at different frequencies.

In Example 14, the medical device lead according to any of Examples 8-13, wherein at least one of the one or more band stop filters is proximate the distal end of the conductor.

In Example 15, a medical device includes a pulse generator and a lead including an electrode configured to contact tissue in a coronary vessel. A lead conductor connects the pulse generator with the electrode, and one or more band stop filters are each coupled to the lead conductor. Each band stop filter includes a conductive element having a length, a first end, and a second end. At least a portion of the conductive element forms a conductive coil. The length of each conductive element is such that, at magnetic resonance imaging (MRI) frequencies, the band stop filter phase shifts an MRI-induced signal on the conductor by 180° to attenuate the MRI-induced signal on the conductor.

In Example 16, the medical device according to Example 15, wherein at least one of the one or more band stop filters is coupled to the lead conductor at either the first end or the second end, and wherein the length of the at least one of the one or more band stop filters is about one quarter wavelength of the MRI-induced signal on the lead conductor.

In Example 17, the medical device according to either Example 15 or 16, wherein at least one of the one or more band stop filters is coupled to the lead conductor at both the first end and second end, and wherein the length of the at least one of the one or more band stop filters is about one half wavelength of the MRI-induced signal on the lead conductor minus a length to account for a propagation delay through the lead conductor between the first and second ends.

In Example 18, the medical device according to any of Examples 15-17, wherein the conductive coil of the band stop filter is coaxial with the lead conductor.

In Example 19, the medical device according to any of Examples 15-18, wherein the conductive coil of the band stop filter is co-radial with the lead conductor.

In Example 20, the medical device according to any of Examples 15-19, wherein the one or more band stop filters comprises at least two band stop filters configured to attenuate MRI-induced signals at different frequencies.

In Example 21, the medical device according to any of Examples 15-20, wherein at least one of the one or more band stop filters is proximate the distal end of the lead conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 is a side view of a coiled lead conductor with a co-radial coiled band stop filter connected at one end according to an embodiment of the present invention.

FIG. 5 is a side view of a cable lead conductor including a coaxial coiled band stop filter connected at one end according to an embodiment of the present invention.

FIG. 6 is a side view of a coiled lead conductor including coaxial coiled band stop filters connected at proximal and distal ends of the conductor according to an embodiment of the present invention.

Figure 1:
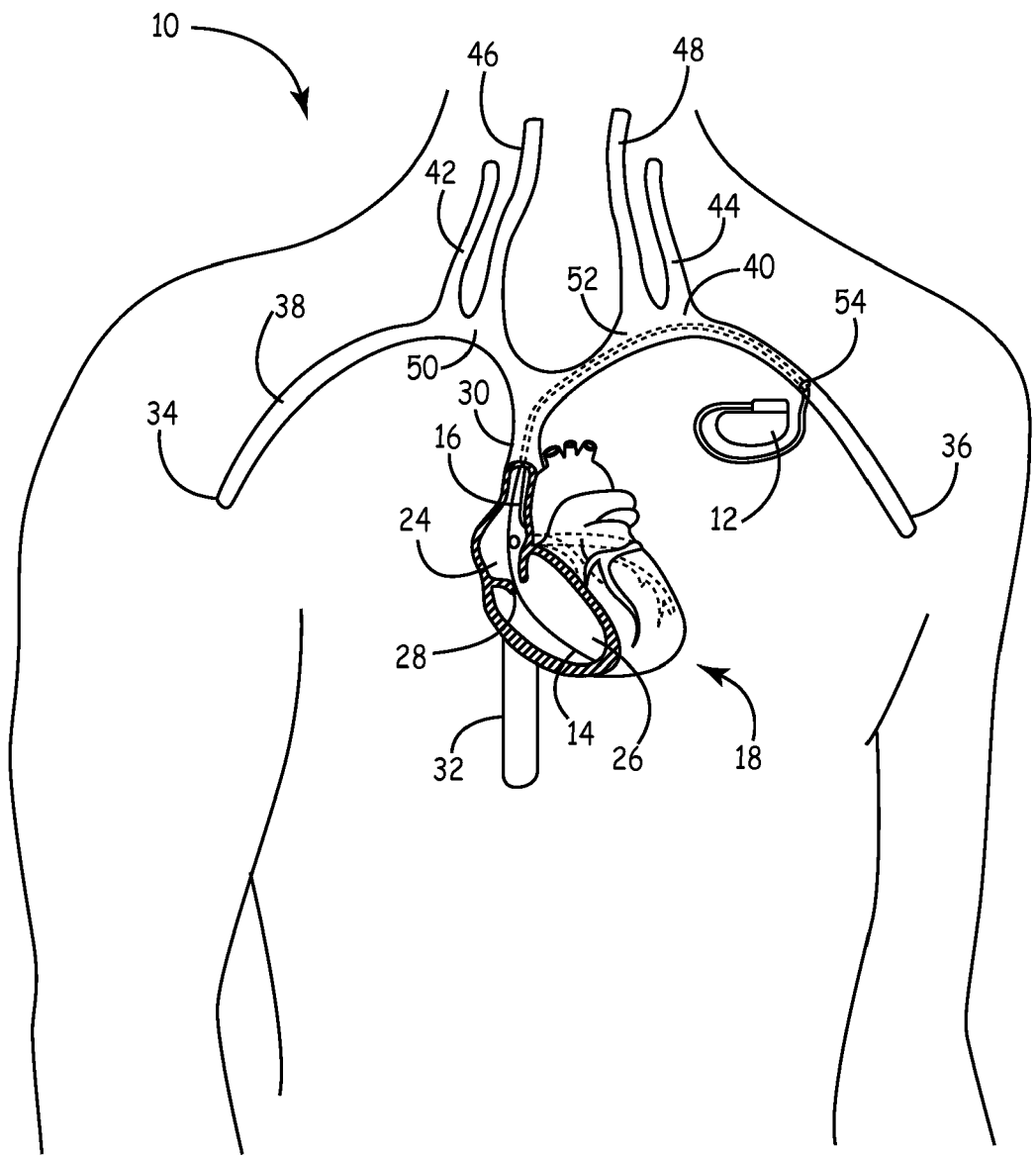
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end. In an MRI environment, the electromagnetic radiation produced by the MRI system may be picked up by conductors of the leads 14, 16. This energy may be transferred through the leads 14, 16 to the electrode in contact with the tissue, which may lead to elevated temperatures at the point of contact. The present invention relates to coiled band stop filters associated with the lead conductors that are configured to attenuate signals on the lead conductors at MRI frequencies.

Figure 2:
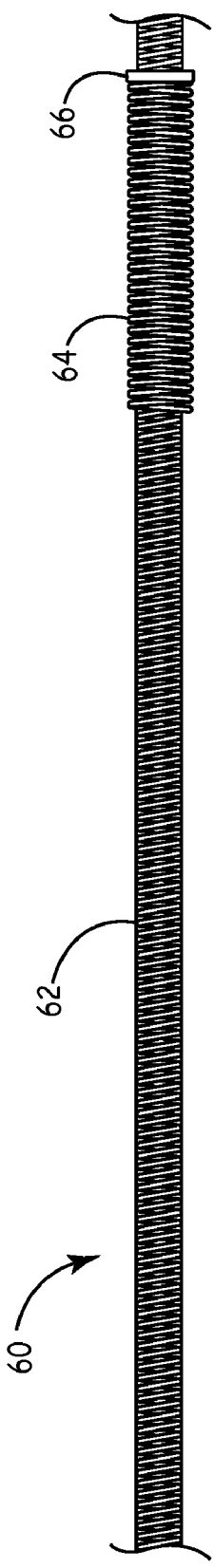
FIG. 2 is a side view of a coiled lead conductor including a coaxial coiled band stop filter connected at one end according to an embodiment of the present invention.

FIG. 2 is a side view of a distal portion of a conductor assembly 60 according to an embodiment of the present invention. The conductor assembly 60 includes a conductive coil 62 and a coiled band stop filter 64. The conductive coil 62 may be configured to extend through the lead 14 and/or the lead 16 shown in FIG. 1. For ease of description, the following description will relate to the conductor assembly 60 in the lead 14, but the same properties for the conductor assembly 60 are applicable for lead 16. The conductive coil 62 is adapted for connection to the pulse generator 12 at the proximal end of the lead 14. In some embodiments, the conductive coil 62 is coupled to a proximal connector at the proximal end of the lead 14. The connector at the proximal end of the lead 14 is sized and shaped to interface with a connector block or other component of the pulse generator 12. While a single conductive coil 62 is shown, the conductor assembly 60 may include a plurality of coaxial or co-radial conductive coils 62 each capable of delivering signals having different characteristics and purposes.

The conductive coil 62 may be coupled to one or more electrodes at the distal end of the conductive coil 62 that deliver the signals carried by the conductive coil 62 to cardiac tissue. The conductive coil 62 may be formed around an insulative core layer (not shown) that defines a lumen sized and shaped to receive a guide wire or stylet employed during implantation of the lead 14. The conductive coil 62 and the band stop filter 64 may be surrounded by an insulative layer (not shown) to insulate the conductive coil 62 and band stop filter 64 from other elements of the lead 14. In some embodiments, the insulative layer extends from the proximal end to the distal end of the lead 14. The insulative layer may be comprised of, for example, silicone material, Teflon, expanded tetrafluoroethylene (eTFE), polytetrafluoroethylene (PTFE), or another suitable non-conductive material.

The band stop filter 64 is connected to the coiled conductive coil 62 via a coupling element 66. In the embodiment shown, the coiled band stop filter 64 is connected to the conductive coil 62 only near the distal end of the band stop filter 64, while the proximal end of the band stop filter 64 is open. In other embodiments, the band stop filter 64 is connected to the conductive coil 62 only at the proximal end of the band stop filter 64. The band stop filter 64 includes a helically wound coil that is arranged coaxially with the conductive coil 62. As will be shown in the other embodiments described herein, the band stop filter 64 may have other configurations and arrangements, and may be disposed at other locations along the conductive coil 62. The band stop filter 64 may be electrically isolated from the conductive coil 62 (except at coupling element 66) with a layer of insulative material.

The band stop filter 64 is configured such that current induced on the conductive coil 62, such as by an applied magnetic field in an MRI environment, is attenuated. In particular, the band stop filter 64 has a length such that, at MRI frequencies, MRI-induced signals on the conductive coil 62 are phase shifted by 180° by the band stop filter 64 to attenuate the MRI-induced signal on the conductive coil 62. In some embodiments, the band stop filter 64 may be disposed adjacent the lead electrodes (e.g., the ring or tip electrode). The attenuation of the MRI-induced signal reduces the amount of heating at electrodes and other exposed conductive elements on the lead 14 and minimizes the effect of MRI induced currents on the pacing and/or therapy signal carried by the conductive coil 62.

Figure 3:
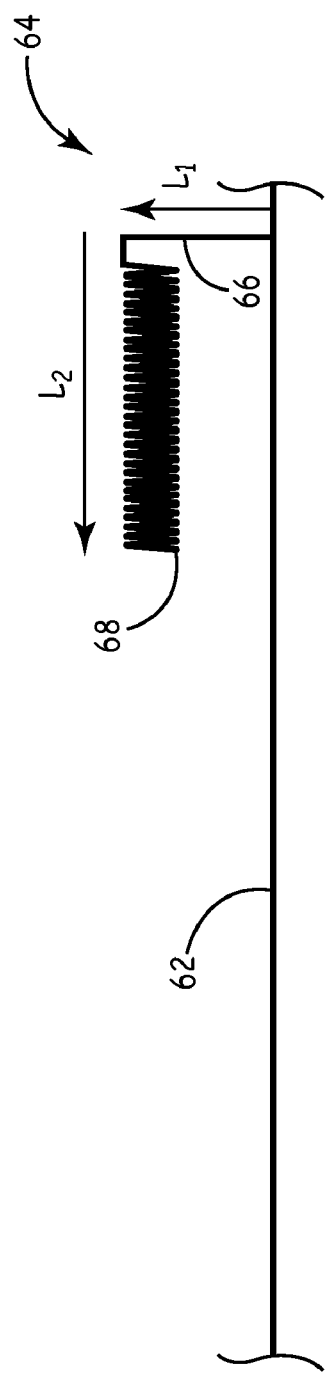
FIG. 3 is a schematic view of a lead conductor with a coiled band stop filter connected at one end according to embodiment of the present invention.

FIG. 3 is a schematic view of the conductor assembly 60 shown in FIG. 2, illustrating characteristics of the band stop filter 64 that provide attenuation of MRI-induced signals on the conductive coil 62. The band stop filter 64 includes a coiled portion 68 that is connected to the conductive coil 62 by the coupling element 66. The coiled portion 68 is comprised of a filar of conductive material that is formed into a coil. The coupling element 66 has a length $L_1$ and the filar of conductive material of the coiled portion 68 has a length $L_2$. The coiling of the filar in the coiled portion 68 minimizes the length of the band stop filter 64 along the longitudinal axis of the lead 14.

An MRI-induced signal on the conductive coil 62 propagates through the band stop filter 64, is reflected by the open proximal end of the band stop filter 64, and is returned to the conductive coil 62. Thus, in order to produce a signal from the band stop filter 64 that is 180° out of phase with the MRI-induced signal on the conductive coil 62, the total length $L_1+L_2$ of the conductive element of the band stop filter 64 is about one-quarter wavelength ($\lambda/4$) of the MRI-induced signal on the conductive coil 62. With this configuration, the total distance the signal propagates through the band stop filter 64 is about one-half wavelength ($\lambda/2$) of the MRI-induced signal on the conductive coil 62. When the phase-shifted signal is provided to the conductive coil 62 by the band stop filter 64, the phase-shifted signal substantially cancels the MRI-induced signal on the conductive coil 62, effectively filtering the MRI-induced signal. In embodiments in which the band stop filter 64 is disposed a lead electrode, the MRI-induced signal is attenuated at or near the electrode.

The total length $L_1+L_2$ of the conductive element of the band stop filter 64 is selected to filter MRI-induced signals at particular frequencies. The total length is also a factor of the dielectric constant surrounding the conductor assembly 60, which affects the speed at which the signals travel through the conductor assembly 60. The speed of the signals through the conductor may be a function of the thickness and material of the insulation surrounding the conductor assembly 60.

For example, a 64 MHz time-varying field may be employed in a 1.5 T MRI system. In a lead environment, the wavelength of a 64 MHz signal may be between about 20 cm and about 60 cm, depending on the thickness of the insulation. Thus, in some embodiments, the total length $L_1+L_2$ of the conductive element of the band stop filter 64 is about 5-15 cm (i.e., one-quarter wavelength) to attenuate the signal induced on the conductive coil 62 by the 64 MHz time-varying field. As another example, a 128 MHz varying field may be employed in a 3 T MRI system. In a lead environment, the wavelength of a 128 MHz signal may be between about 10 cm and about 30 cm, depending on the thickness of the insulation. Thus, in some embodiments, the total length $L_1+L_2$ of the conductive element of the band stop filter 64 is about 2.5-7.5 cm (one-quarter wavelength) to attenuate the signal induced on the conductive coil 62 by the 128 MHz time-varying field.

As discussed above, the band stop filter may have other characteristics and configurations, and may be associated with other types of lead conductors. For example, FIG. 4 is a side view of a distal portion of a conductor assembly 70 according to another embodiment of the present invention. The conductor assembly 70 includes a conductive coil 72 and a coiled band stop filter 74. The conductive coil 72 may be configured to extend through the lead 14 and/or the lead 16 shown in FIG. 1. The conductive coil 72 is adapted for connection to the pulse generator 12 at the proximal end of the lead 14 and/or lead 16. In some embodiments, the conductive coil 72 is coupled to a proximal connector at the proximal end of the lead 14 and/or lead 16. The connector at the proximal end of the lead 14 and/or lead 16 is sized and shaped to interface with a connector block or other component of the pulse generator 12.

The conductive coil 72 may be coupled to one or more electrodes at the distal end of the conductive coil 72 that deliver the signals carried by the conductive coil 72 to cardiac tissue. The conductive coil 72 may be formed around an insulative core layer 75 that defines a lumen sized and shaped to receive a guide wire or stylet employed during implantation of the lead. The conductive coil 72 and the band stop filter 74 may be surrounded by an insulative layer (not shown) to insulate the conductive coil 72 and band stop filter 74 from other elements of the lead.

The band stop filter 74 is connected to the conductive coil 72 via a coupling element 76. In the embodiment shown, the coiled band stop filter 74 is connected to the conductive coil 72 only near the distal end of the band stop filter 74, while the proximal end of the band stop filter 74 is open. In other embodiments, the band stop filter 74 is connected to the conductive coil 72 only at the proximal end of the band stop filter 74. The band stop filter 74 includes a helically wound coil that is arranged co-radially with the conductive coil 72. The band stop filter 74 may be electrically isolated from the conductive coil 72 (except at coupling element 76) with insulative material.

Similar to the embodiment shown in FIGS. 2 and 3, an MRI-induced signal on the conductive coil 72 propagates through the band stop filter 74, is reflected by the open proximal end of the band stop filter 74, and is returned to the conductive coil 72. Thus, in order to produce a signal from the band stop filter 74 that is 180° out of phase with the MRI-induced signal on the conductive coil 72, the total length of the conductive element of the band stop filter 74 is about one-quarter wavelength ($\lambda/4$) of the MRI-induced signal on the conductive coil 72. With this configuration, the total distance the signal propagates through the band stop filter 74 is about one-half wavelength ($\lambda/2$) of the MRI-induced signal on the conductive coil 72. When the phase-shifted signal is provided to the conductive coil 72 by the band stop filter 74, the phase-shifted signal substantially cancels the MRI-induced signal on the conductive coil 72, effectively filtering the MRI-induced signal. The total length of the conductive element of the band stop filter 74 is selected to filter MRI-induced signals at frequencies associated with MRI environments.

FIG. 5 is a side view of a distal portion of a conductor assembly 80 according to another embodiment of the present invention. The conductor assembly 80 includes a conductive cable 82 and a coiled band stop filter 84. The conductive cable 82 may be configured to extend through the lead 14 and/or the lead 16 shown in FIG. 1. The conductive cable 82 is adapted for connection to the pulse generator 12 at the proximal end of the lead 14 and/or lead 16. In some embodiments, the conductive cable 82 is coupled to a proximal connector at the proximal end of the lead 14 and/or lead 16. The connector at the proximal end of the lead 14 and/or lead 16 is sized and shaped to interface with a connector block or other component of the pulse generator 12. The conductive cable 82 may be configured to deliver a high voltage defibrillation signal from the pulse generator 12 to a defibrillation coil that depolarizes a critical mass of the heart muscle, terminates an arrhythmia, and allows normal sinus rhythm to be reestablished in the sinoatrial node of the heart 18.

The band stop filter 84 is connected to the conductive cable 82 via a coupling element 86. In the embodiment shown, the band stop filter 84 is connected to the conductive cable 82 only near the distal end of the band stop filter 84, while the proximal end of the band stop filter 84 is open. In other embodiments, the band stop filter 84 is connected to the conductive cable 82 only at the proximal end of the band stop filter 84. The band stop filter 84 includes a helically wound coil that is arranged around the conductive cable 82. The band stop filter 84 may be electrically isolated from the conductive cable 82 (except at coupling element 86) with insulative material.

Similar to the embodiments described above, an MRI-induced signal on the conductive cable 82 propagates through the band stop filter 84, is reflected by the open proximal end of the band stop filter 84, and is returned to the conductive cable 82. Thus, in order to produce a signal from the band stop filter 84 that is 180° out of phase with the MRI-induced signal on the conductive cable 82, the total length of the conductive element of the band stop filter 84 is about one-quarter wavelength ($\lambda/4$) of the MRI-induced signal on the conductive cable 82. Thus, the total distance the signal propagates through the band stop filter 84 is about one-half wavelength ($\lambda/2$) of the MRI-induced signal on the conductive cable 82. When the phase-shifted signal is provided to the conductive cable 82 by the band stop filter 84, the phase-shifted signal substantially cancels the MRI-induced signal on the conductive cable 82, effectively filtering the MRI-induced signal. The total length of the conductive element of the band stop filter 84 is selected to filter MRI-induced signals at frequencies associated with MRI environments.

In some cases, it may also be desirable to filter MRI-induced signals at the proximal end of the lead, such as to reduce heating of the can of the pulse generator 12. FIG. 6 is a side view of a conductor assembly 90 according to another embodiment of the present invention, including proximal portion 90a and distal portion 90b. The conductor assembly 90 includes a conductive coil 92 and proximal coiled band stop filter 94a and distal coiled band stop filter 94b. The conductive coil 92 may be configured to extend through the lead 14 and/or the lead 16 shown in FIG. 1. The conductive coil 92 is adapted for connection to the pulse generator 12 at the proximal end of the lead 14 and/or lead 16. In some embodiments, the conductive coil 92 is coupled to a proximal connector at the proximal end of the lead 14 and/or lead 16. The connector at the proximal end of the lead 14 and/or lead 16 is sized and shaped to interface with a connector block or other component of the pulse generator 12.

The conductive coil 92 may be coupled to one or more electrodes at the distal end of the conductive coil 92 that deliver the signals carried by the conductive coil 92 to cardiac tissue. The conductive coil 92 may be formed around an insulative core layer (not shown) that defines a lumen sized and shaped to receive a guide wire or stylet employed during implantation of the lead. The conductive coil 92 and the band stop filters 94a and 94b may be surrounded by an insulative layer (not shown) to insulate the conductive coil 92 and band stop filters 94a and 94b from other elements of the lead 14.

The band stop filter 94a is connected to the conductive coil 92 via a coupling element 96a, and the band stop filter 94b is connected to the conductive coil 92 via a coupling element 96b. In the embodiment shown, the coiled band stop filter 94a is connected to the conductive coil 92 only near the proximal end of the band stop filter 94a (proximate to the pulse generator 12), and the coiled band stop filter 94b is connected to the conductive coil 92 only near the distal end of the band stop filter 94b (proximate the distal electrodes). In other embodiments, the band stop filter 94a is connected to the conductive coil 92 only at the distal end of the band stop filter 94a and/or the band stop filter 94b is connected to the conductive coil 92 only at the distal end of the band stop filter 94b. The band stop filters 94a and 94b each include a helically wound coil that is arranged co-axially with the conductive coil 92. The band stop filters 94a and 94b may be electrically isolated from the conductive coil 92 (except at coupling elements 96a and 96b) with insulative material.

Similar to the embodiment described above, an MRI-induced signal on the conductive coil 92 propagates through the band stop filters 94a and 94b, is reflected by the open proximal ends of the band stop filters 94a and 94b, and is returned to the conductive coil 92. Thus, in order to produce signals from the band stop filters 94a and 94b that is 180° out of phase with the MRI-induced signal on the conductive coil 92, the total length of each conductive element of the band stop filters 94a and 94b is about one-quarter wavelength ($\lambda/4$) of the MRI-induced signal on the conductive coil 92. With this configuration, the total distance the signal propagates through the band stop filters 94a and 94b is about one-half wavelength ($\lambda/2$) of the MRI-induced signal on the conductive coil 92. When the phase-shifted signal is provided to the conductive coil 92 by the band stop filters 94a and 94b, the phase-shifted signal substantially cancels the MRI-induced signal on the conductive coil 92, effectively filtering the MRI-induced signal. The total length of each conductive element of the band stop filters 94a and 94b is selected to filter MRI-induced signals at frequencies associated with MRI environments. It should be noted that while the embodiment shown in FIG. 6 includes two band stop filters 94a and 94b, one or more additional band stop filters may be arranged periodically or aperiodically along the length of the conductive coil 92.

Figure 7:
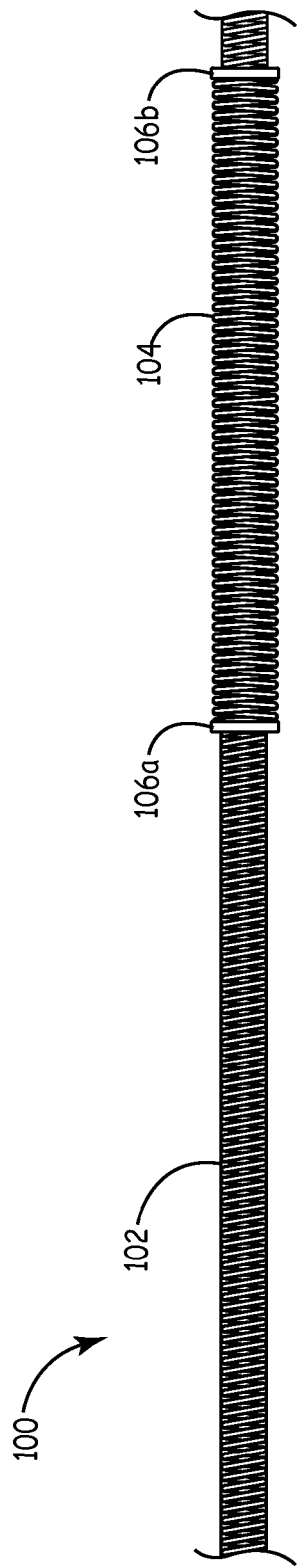
FIG. 7 is a side view of a coiled lead conductor including a coaxial coiled band stop filter connected in parallel according to an embodiment of the present invention.

FIG. 7 is a side view of a distal portion of a conductor assembly 100 according to another embodiment of the present invention. The conductor assembly 100 includes a conductive coil 102 and a coiled band stop filter 104. The conductive coil 102 may be configured to extend through the lead 14 and/or the lead 16 shown in FIG. 1. The conductive coil 102 is adapted for connection to the pulse generator 12 at the proximal end of the lead 14 and/or lead 16. In some embodiments, the conductive coil 102 is coupled to a proximal connector at the proximal end of the lead 14 and/or lead 16. The connector at the proximal end of the lead 14 and/or lead 16 is sized and shaped to interface with a connector block or other component of the pulse generator 12.

The conductive coil 102 may be coupled to one or more electrodes at the distal end of the conductive coil 102 that deliver the signals carried by the conductive coil 102 to cardiac tissue. The conductive coil 102 may be formed around an insulative core layer (not shown) that defines a lumen sized and shaped to receive a guide wire or stylet employed during implantation of the lead. The conductive coil 102 and the band stop filter 104 may be surrounded by an insulative layer (not shown) to insulate the conductive coil 102 and band stop filter 104 from other elements of the lead.

The band stop filter 104 is connected to the coiled conductive coil 102 via coupling elements 106a and 106b. In the embodiment shown, the band stop filter 104 is connected to the conductive coil 102 at both the proximal and distal ends of the band stop filter 104. The band stop filter 104 includes a helically wound coil that is arranged coaxially with the conductive coil 102. The band stop filter 104 may be electrically isolated from the conductive coil 102 (except at coupling elements 106a and 106b) with a layer of insulative material.

The band stop filter 104 is configured such that current induced on the conductive coil 102, such as by an applied magnetic field in an MRI environment, is attenuated. In particular, the band stop filter 104 has a length such that, at MRI frequencies, MRI-induced signals on the conductive coil 102 are phase shifted by 180° by the band stop filter 104 to attenuate the MRI-induced signal on the conductive coil 102. This reduces the amount of heating at electrodes and other exposed conductive elements on the lead and minimizes the effect of MRI induced currents on the pacing and/or therapy signal carried by the conductive coil 102.

Figure 8:
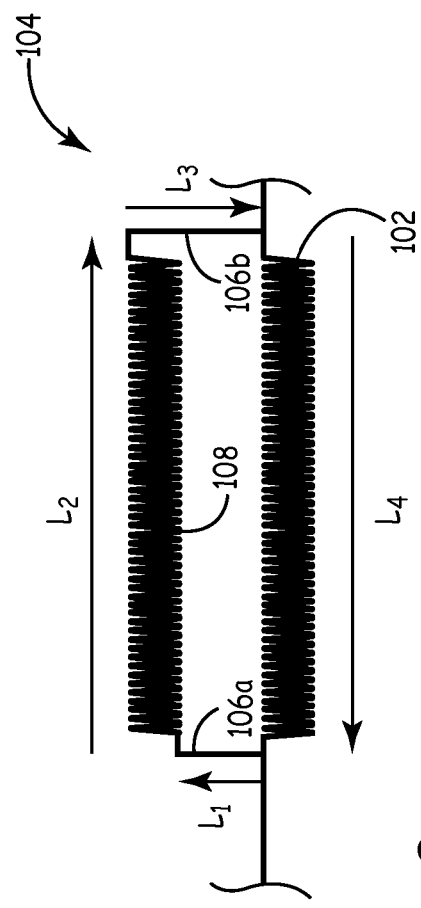
FIG. 8 is a schematic view of a coiled lead conductor with a coiled band stop filter connected in parallel according to an embodiment of the present invention.

FIG. 8 is a schematic view of the conductor assembly 100 shown in FIG. 7, illustrating characteristics of the band stop filter 104 that provide attenuation of MRI-induced signals on the conductive coil 102. The band stop filter 104 includes a coiled portion 108 that is connected to the conductive coil 102 by the coupling elements 106a and 106b. The coiled portion 108 is comprised of a filar of conductive material that is formed into a coil. The coupling element 106a has a length $L_1$, the filar of conductive material of the coiled portion 108 has a length $L_2$, the coupling element 106b has a length $L_3$, and the portion of the conductive coil 102 connected between coupling elements 106a and 106b has a length $L_4$. The coiling of the filar in the coiled portion 108 minimizes the length of the band stop filter 104 along the longitudinal axis of the lead.

An MRI-induced signal on the conductive coil 102 propagates through the band stop filter 104 and is returned to the conductive coil 102. Thus, in order to produce a signal from the band stop filter 104 that is 180° out of phase with the MRI-induced signal on the conductive coil 102, the total length $L_1+L_2+L_3+L_4$ of the conductive element of the band stop filter 104 with the conductive coil 102 between coupling elements 106a and 106b is about one-half wavelength ($\lambda/2$) of the MRI-induced signal on the conductive coil 102. In other words, the propagation delay through the band stop filter 104 is such that the signal after traveling through the band stop filter 104 and the portion of the conductive coil 102 between the coupling elements 106a, 106b is 180° out of phase with the signal on the conductive coil 102. When the phase-shifted signal is returned to the conductive coil 102, the phase-shifted signal substantially cancels the MRI-induced signal on the conductive coil 102, effectively filtering the MRI-induced signal.

Figure 9:
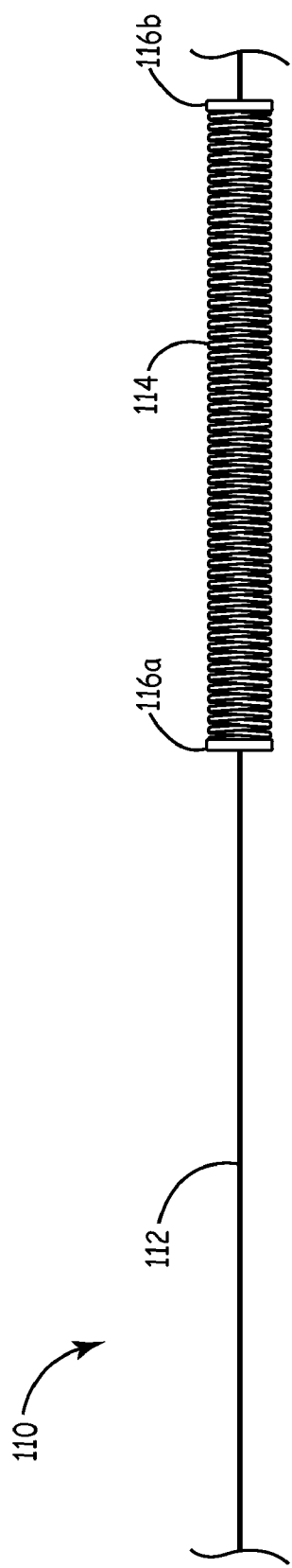
FIG. 9 is a side view of a cable lead conductor including a coaxial coiled band stop filter connected in parallel according to an embodiment of the present invention.

FIG. 9 is a side view of a distal portion of a conductor assembly 110 according to another embodiment of the present invention. The conductor assembly 110 includes a conductive cable 112 and a coiled band stop filter 114. The conductive cable 112 may be configured to extend through the lead 14 and/or the lead 16 shown in FIG. 1. The conductive cable 112 is adapted for connection to the pulse generator 12 at the proximal end of the lead 14 and/or lead 16. In some embodiments, the conductive cable 112 is coupled to a proximal connector at the proximal end of the lead 14 and/or lead 16. The connector at the proximal end of the lead 14 and/or lead 16 is sized and shaped to interface with a connector block or other component of the pulse generator 12. The conductive cable 112 may be configured to deliver a high voltage defibrillation signal from the pulse generator 12 to a defibrillation coil that depolarizes a critical mass of the heart muscle, terminates an arrhythmia, and allows normal sinus rhythm to be reestablished in the sinoatrial node of the heart 18.

Figure 10:
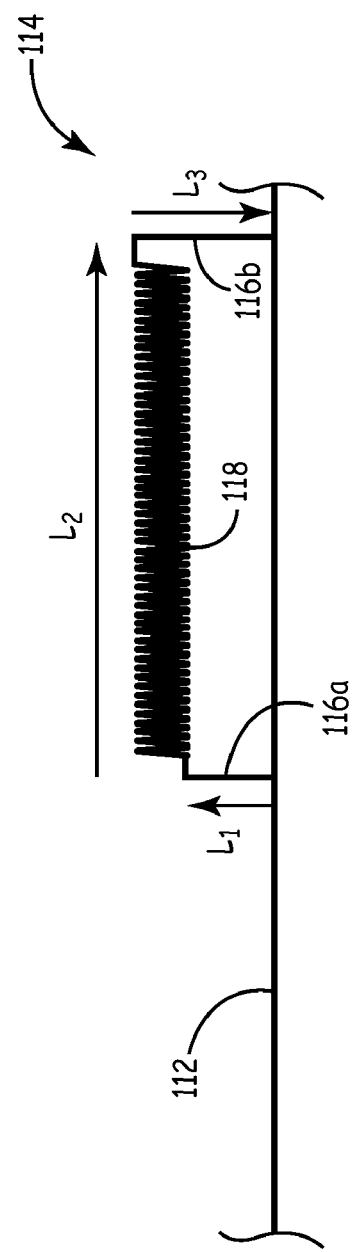
FIG. 10 is a schematic view of a cable lead conductor with a coiled band stop filter connected in parallel according to an embodiment of the present invention.

FIG. 10 is a schematic view of the conductor assembly 110 shown in FIG. 9, illustrating characteristics of the band stop filter 114 that provide attenuation of MRI-induced signals on the conductive cable 112. The band stop filter 114 is connected to the conductive cable 112 via coupling elements 116a and 116b. In the embodiment shown, the band stop filter 114 is connected to the conductive cable 112 at both the proximal and distal ends of the band stop filter 114. The band stop filter 114 includes a helically wound coil that is arranged around the conductive cable 112. The band stop filter 114 may be electrically isolated from the conductive cable 112 (except at coupling element 116a and 116b) with insulative material.

Similar to the embodiments described above, an MRI-induced signal on the conductive cable 112 propagates through the band stop filter 114 and is returned to the conductive cable 112. Thus, in order to produce a signal from the band stop filter 114 that is 180° out of phase with the MRI-induced signal on the conductive cable 112, the total length $L_1+L_2+L_3$ of the conductive element of the band stop filter 114 is about one-half wavelength ($\lambda/2$) of the MRI-induced signal on the conductive cable 112. When the phase-shifted signal is provided at to the conductive cable 112 by the band stop filter 114, the phase-shifted signal substantially cancels the MRI-induced signal on the conductive cable 112, effectively filtering the MRI-induced signal. The total length of the conductive element of the band stop filter 114 is selected to filter MRI-induced signals at frequencies associated with MRI environments.

Figure 11:
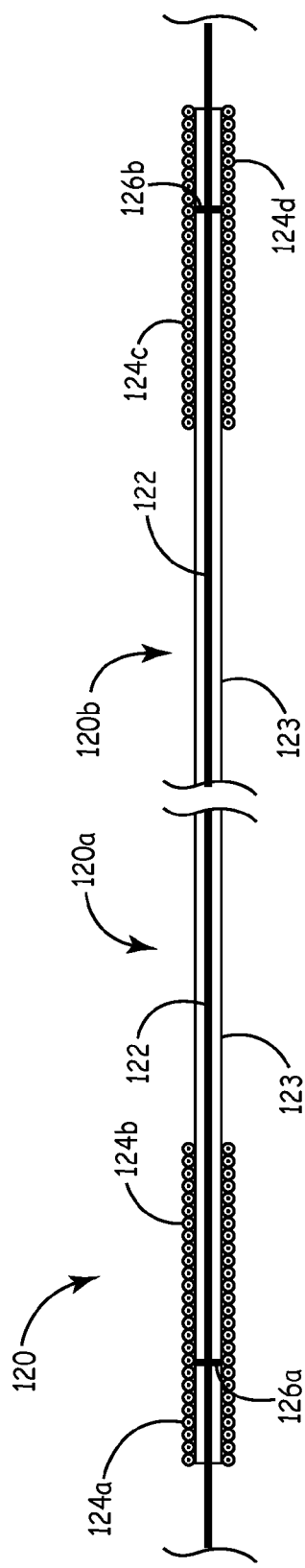
FIG. 11 is a cross-sectional view of a cable lead conductor including coaxial coiled band stop filters tuned for different frequencies connected at proximal and distal ends of the conductor according to an embodiment of the present invention.

In some cases, it may be desirable to incorporate band stop filters tuned to different frequencies into the same lead to provide attenuation of MRI-induced signals in different MRI environments (e.g., 1.5 T and 3 T MRI environments). FIG. 11 is a side view of a conductor assembly 120 according to another embodiment of the present invention, including proximal portion 120a and distal portion 120b. The conductor assembly 120 includes a conductor 122, insulating layer 123, proximal coiled band stop filters 124a and 124b and distal coiled band stop filters 124c and 124d. The conductor 122, which may be configured as a conductive coil or conductive cable, for example, may be configured to extend through the lead 14 and/or the lead 16 shown in FIG. 1. The conductor 122 is adapted for connection to the pulse generator 12 at the proximal end of the lead 14 and/or lead 16. In some embodiments, the conductor 122 is coupled to a proximal connector at the proximal end of the lead 14 and/or lead 16. The connector at the proximal end of the lead 14 and/or lead 16 is sized and shaped to interface with a connector block or other component of the pulse generator 12.

The band stop filters 124a and 124b are connected to the conductor 122 via a coupling element 126a, and the band stop filters 124c and 124d are connected to the conductor 122 via a coupling element 126b. In other embodiments, each of band stop filters 124a, 124b, 124c, and 124d is connected by a separate coupling element 126. The band stop filters 124a, 124b, 124c, and 124d each includes a helically wound coil that is arranged co-axially with the conductor 122. The band stop filters 124a, 124b, 124c, and 124d are electrically isolated from the conductor 122 (except at coupling elements 126a and 126b) with insulative material.

In the embodiment shown in FIG. 11, the band stop filters 124a and 124d are configured to attenuate MRI-induced signals on the conductor 122 at a first frequency, and the band stop filters 124b and 124c are configured to attenuate MRI-induced signals on the conductor 122 at a second frequency. Since the band stop filters 124a, 124b, 124c, and 124d are each open on one end, the length of the conductive elements of band stop filters 124a and 124d is about one-quarter wavelength ($\lambda_1/4$) of the MRI-induced signal to be attenuated on the conductor 122 at the first frequency, and the length of the conductive elements of band stop filters 124b and 124c is about one-quarter wavelength ($\lambda_2/4$) of the MRI-induced signal to be attenuated on the conductor 122 at the first frequency. When the phase-shifted signal is provided to the conductor 122 by the band stop filters 124a and 124b, the phase-shifted signal substantially cancels the MRI-induced signal on the conductor 122, effectively filtering the MRI-induced signal.

In alternative embodiments, one or more of the band stop filters 124a, 124b, 124c, and 124d are connected to the conductor 122 at both ends, with the conductive element having a length of about one-half wavelength ($\lambda/2$) of the MRI-induced signal to be attenuated on the conductor 122 (i.e., $\lambda_1/2$ for band stop filters 124a and 124d, and $\lambda_2/2$ for band stop filters 124b and 124c), minus a length to account for propagation delay through the portions of the conductor 102 between coupling elements of the 124a, 124b, 124c, and 124d.

In summary, the present invention relates to a medical device lead including a conductor and one or more band stop filters. The conductor extends through a lead body and includes a proximal end and a distal end. The one or more band stop filters each has a first end and a second end and includes a conductive coil. At least one of the first end and second end of each band stop filter is coupled to the conductor. A length of each band stop filter is such that, at magnetic resonance imaging (MRI) frequencies, the band stop filter phase shifts an MRI-induced signal on the conductor by 180° to attenuate the MRI-induced signal on the conductor. In some embodiments, the band stop filter is connected at one end to the lead conductor and open on the other end. In such embodiments, the band stop filter may have a length of about one quarter wavelength of the MRI-induced signal on the conductor. In other embodiments, the band stop filter is connected at both ends to the lead conductor. In such embodiments, the band stop filter may have a length of about one-half wavelength of the MRI-induced signal on the conductor. The attenuation of the MRI-induced signal reduces the amount of heating of the electrodes on the lead and the pulse generator.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical device lead comprising:
   a conductor extending through a lead body and including a proximal end and a distal end; and
   one or more band stop filters each having a first end and a second end and including a conductive coil, at least one of the first end and second end of each band stop filter coupled to the conductor, wherein a length of each band stop filter is such that, at magnetic resonance imaging (MRI) frequencies, the band stop filter phase shifts an MRI-induced signal on the conductor by 180° to attenuate the MRI-induced signal on the conductor.

2. The medical device lead of claim 1, wherein at least one of the one or more band stop filters is coupled to the conductor at either the first end or the second end, and wherein the length of the at least one of the one or more band stop filters is about one quarter wavelength of the MRI-induced signal on the conductor.

3. The medical device lead of claim 1, wherein at least one of the one or more band stop filters is coupled to the conductor at both the first end and second end, and wherein the length of the at least one of the one or more band stop filters is about one half wavelength of the MRI-induced signal on the conductor minus a length to account for a propagation delay through the conductor between the first and second ends.

4. The medical device lead of claim 1, wherein the conductive coil of the band stop filter is coaxial with the conductor.

5. The medical device lead of claim 1, wherein the conductive coil of the band stop filter is co-radial with the conductor.

6. The medical device lead of claim 1, wherein the one or more band stop filters comprises at least two band stop filters configured to attenuate MRI-induced signals at different frequencies.

7. The medical device lead of claim 1, wherein at least one of the one or more band stop filters is proximate the distal end of the conductor.

8. A medical device lead comprising:
a lead body including a conductor extending from a proximal end, which is configured to be connected to a pulse generator, to a distal end; and
one or more band stop filters within the lead body each including a conductive element having a length, a first end, and a second end, at least a portion of the conductive element forming a conductive coil, wherein each band stop filter is coupled to the conductor such that an MRI-induced signal on the conductor propagates through the band stop filter a total distance of approximately one-half wavelength of the MRI-induced signal.

9. The medical device lead of claim 8, wherein at least one of the one or more band stop filters is coupled to the conductor at either the first end or the second end, and wherein the length of the conductive element of the at least one of the one or more band stop filters is about one quarter wavelength of the MRI-induced signal on the conductor.

10. The medical device lead of claim 8, wherein at least one of the one or more band stop filters is coupled to the conductor at both the first end and second end, and wherein the length of the conductive element of the at least one of the one or more band stop filters is about one half wavelength of the MRI-induced signal on the conductor minus a length to account for a propagation delay through the conductor between the first and second ends.

11. The medical device lead of claim 8, wherein the conductive coil of the band stop filter is coaxial with the conductor.

12. The medical device lead of claim 8, wherein the conductive coil of the band stop filter is co-radial with the conductor.

13. The medical device lead of claim 8, wherein the one or more band stop filters comprises at least two band stop filters configured to attenuate MRI-induced signals at different frequencies.

14. The medical device lead of claim 8, wherein at least one of the one or more band stop filters is proximate the distal end of the conductor.

15. A medical device, comprising:
a pulse generator; and
a lead including an electrode configured to contact tissue in a coronary vessel, a lead conductor connecting the pulse generator with the electrode, and one or more band stop filters each coupled to the lead conductor, wherein each band stop filter includes a conductive element having a length, a first end, and a second end, at least a portion of the conductive element forming a conductive coil, and wherein the length of each conductive element is such that, at magnetic resonance imaging (MRI) frequencies, the band stop filter phase shifts an MRI-induced signal on the conductor by 180° to attenuate the MRI-induced signal on the conductor.

16. The medical device of claim 15, wherein at least one of the one or more band stop filters is coupled to the lead conductor at either the first end or the second end, and wherein the length of the at least one of the one or more band stop filters is about one quarter wavelength of the MRI-induced signal on the lead conductor.

17. The medical device of claim 15, wherein at least one of the one or more band stop filters is coupled to the lead conductor at both the first end and second end, and wherein the length of the at least one of the one or more band stop filters is about one half wavelength of the MRI-induced signal on the lead conductor minus a length to account for a propagation delay through the lead conductor between the first and second ends.

18. The medical device of claim 15, wherein the conductive coil of the band stop filter is coaxial with the lead conductor.

19. The medical device of claim 15, wherein the conductive coil of the band stop filter is co-radial with the lead conductor.

20. The medical device of claim 15, wherein the one or more band stop filters comprises at least two band stop filters configured to attenuate MRI-induced signals at different frequencies.

21. The medical device of claim 15, wherein at least one of the one or more band stop filters is proximate the distal end of the lead conductor.

* * * * *